(12) United States Patent
Fitzpatrick

(10) Patent No.: US 8,536,235 B2
(45) Date of Patent: Sep. 17, 2013

(54) METHANOL PROCESS

(75) Inventor: Terence James Fitzpatrick, Middlesbrough (GB)

(73) Assignee: Johnson Matthey PLC, London (GB)

( * ) Notice: Subject to any disclaimer, the term of this patent is extended or adjusted under 35 U.S.C. 154(b) by 864 days.

(21) Appl. No.: 12/602,004

(22) PCT Filed: May 6, 2008

(86) PCT No.: PCT/GB2008/050332
§ 371 (c)(1),
(2), (4) Date: Nov. 25, 2009

(87) PCT Pub. No.: WO2008/146032
PCT Pub. Date: Dec. 4, 2008

(65) Prior Publication Data
US 2010/0160694 A1   Jun. 24, 2010

(30) Foreign Application Priority Data

May 25, 2007   (GB) .................................. 0710022.5

(51) Int. Cl.
*C07C 27/00* (2006.01)
(52) U.S. Cl.
USPC ........................................................ 518/713
(58) Field of Classification Search
USPC ........................................................ 518/713
See application file for complete search history.

(56) References Cited

U.S. PATENT DOCUMENTS

| 4,788,175 A | 11/1988 | Short et al. |
| 5,631,302 A | 5/1997 | Konig et al. |
| 5,827,901 A | 10/1998 | Konig et al. |

FOREIGN PATENT DOCUMENTS

| DE | 33 37 228 | 4/1985 |
| WO | WO 2005/115607 | 12/2005 |

OTHER PUBLICATIONS

International Search Report for International Application No. PCT/GB/050332 mailed on Oct. 23, 2008.

*Primary Examiner* — Elvis O Price
(74) *Attorney, Agent, or Firm* — RatnerPrestia

(57) ABSTRACT

A process for the synthesis of methanol comprises: (a) passing a synthesis gas mixture comprising a loop gas and a make-up gas through a first synthesis reactor containing a methanol synthesis catalyst, said reactor cooled by boiling water under pressure, to form a mixed gas containing methanol, (b) cooling the mixed gas containing methanol, (c) passing said cooled mixed gas containing methanol through a second synthesis reactor containing a methanol synthesis catalyst in which further methanol is synthesized to form a product gas stream, (d) cooling said product gas to condense methanol, (e) recovering said methanol and returning unreacted gas as the loop gas to said first synthesis reactor, wherein the mixed gas containing methanol from the first synthesis reactor is cooled in heat exchange with either said loop gas or said make up gas.

15 Claims, 3 Drawing Sheets

METHANOL PROCESS

CROSS-REFERENCE TO RELATED APPLICATIONS

This application is the U.S. National Phase application of PCT International Application No. PCT/GB2008/050332, filed May 6, 2008, and claims priority of British Patent Application No. 0710022.5, filed May 25, 2007, both of which are incorporated herein by reference.

FIELD OF THE INVENTION

This invention relates to a process for synthesising methanol.

BACKGROUND OF THE INVENTION

Methanol synthesis is generally performed by passing a synthesis gas comprising hydrogen, carbon oxides and any inert gases at an elevated temperature and pressure through one or more beds of a methanol synthesis catalyst, which is often a copper-containing composition. Methanol is generally recovered by cooling the product gas stream to below the dew point of the methanol and separating off the product as a liquid. The crude methanol is typically purified by distillation. The process is often operated in a loop: thus the remaining unreacted gas stream is usually recycled to the synthesis reactor as part of the synthesis gas via a circulator. Fresh synthesis gas, termed make-up gas, is added to the recycled unreacted gas to form the synthesis gas stream. A purge stream is often taken from the circulating gas stream to avoid the build up of inert gasses.

U.S. Pat. No. 5,631,302 describes a process in which methanol is catalytically produced from a synthesis gas containing hydrogen and carbon oxides on copper-containing catalysts under pressures in the range from 20 to 20 bars and at temperatures in the range from 200 to 350 DEG C. The synthesis gas is passed through a first synthesis reactor, which consists of a shaft reactor and contains a fixed bed of a copper-containing catalyst. The reaction in the shaft reactor is carried out adiabatically and without a recycling of synthesis gas. Together with recycle gas, the gas mixture which has not been reacted in the first synthesis reactor is passed through a second synthesis reactor, which contains a copper-containing catalyst, which is disposed in tubes and is indirectly cooled through boiling water.

U.S. Pat. No. 5,827,901 describes a process in which methanol is catalytically produced from a synthesis gas containing hydrogen and carbon oxides on copper-containing catalysts at pressures in the range 20 to 120 bar and temperatures in the range 130 DEG to 350 DEG C. The synthesis gas is first of all passed through a first synthesis reactor, in which the catalyst is provided in tubes surrounded by water as a coolant, which is boiling at an elevated pressure. From the first reactor a first mixture containing gases and methanol vapour is withdrawn and passed without cooling through a second synthesis reactor. In the second reactor the catalyst is cooled with synthesis gas to which a make up gas has been added.

SUMMARY OF THE INVENTION

There is a need for more compact, more efficient arrangements, in particular where the synthesis gas has a high carbon monoxide to carbon dioxide ratio.

Accordingly the invention provides a process for the synthesis of methanol comprising the steps of:
(a) passing a synthesis gas mixture comprising a loop gas and a make-up gas through a first synthesis reactor containing a methanol synthesis catalyst, said reactor cooled by boiling water under pressure, to form a mixed gas containing methanol,
(b) cooling the mixed gas containing methanol,
(c) passing said cooled mixed gas containing methanol through a second synthesis reactor containing a methanol synthesis catalyst in which further methanol is synthesised to form a product gas stream,
(d) cooling said product gas to condense methanol,
(e) recovering said methanol and returning unreacted gas as the loop gas to said first synthesis reactor,
wherein the mixed gas containing methanol from the first synthesis reactor is cooled in heat exchange with either said loop gas or said make up gas.

BRIEF DESCRIPTION OF THE DRAWINGS

The invention will be further described by reference to the figures in which.

DETAILED DESCRIPTION OF THE INVENTION

Figure 1:
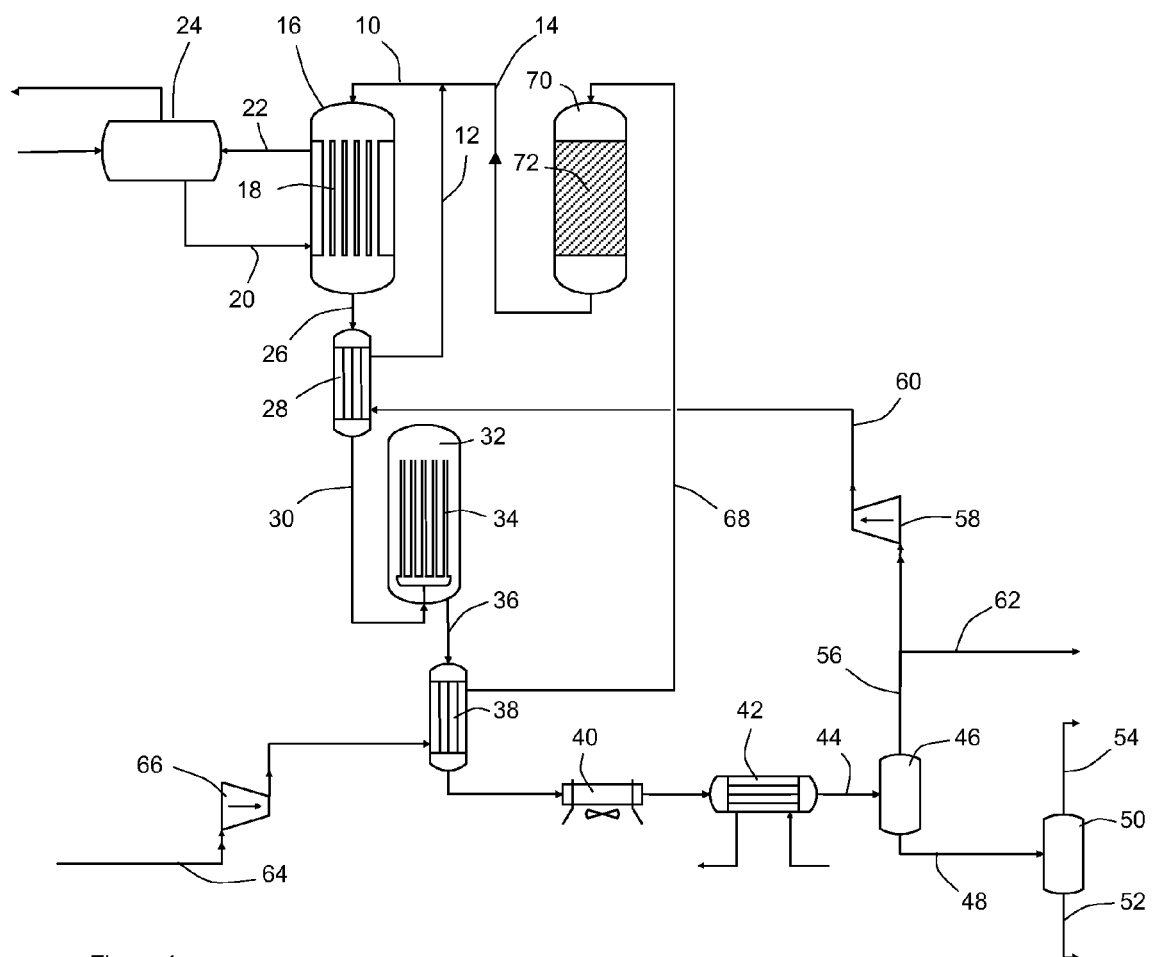
FIG. 1 depicts a flowsheet according to one embodiment of the present invention utilising a SRC and TCC.

In the present invention the synthesis gas used as make up gas may be generated by the steam reforming of methane or naphtha using established steam reforming processes, including pre-reforming. However the present invention is of particular effectiveness in utilising so-called "reactive synthesis gases" generated by processes including a step of partial oxidation of a hydrocarbon or carbonaceous feedstock. By "reactive synthesis gases" we mean a synthesis gas comprising hydrogen, carbon monoxide and carbon dioxide in which the ratio (by volume) of carbon monoxide to carbon dioxide is $\geq 2:1$, preferably $\geq 5:1$. Such processes include combined reforming in which a first portion of a hydrocarbon feedstock is subjected to steam reforming and a second portion is subjected to autothermal reforming; and from coal gasification. Alternatively, off-gases from refineries or other chemical processes comprising principally hydrogen and carbon oxides (mainly as carbon monoxide) may also be used. The table below gives typical synthesis gas compositions from steam reforming combined reforming and coal gasification.

| % v/v | Steam Reforming | Combined Reforming | Coal Gasification |
|---|---|---|---|
| $H_2$ | 70.33 | 67.54 | 67.62 |
| CO | 14.43 | 22.57 | 28.56 |
| $CO_2$ | 10.35 | 7.59 | 2.97 |
| $CH_4$ | 3.51 | 2.17 | 0.11 |
| $N_2$ | 1.38 | 0.02 | 0.51 |
| Ar | 0.00 | 0.10 | 0.23 |

Because the final temperature in autothermal reforming is higher than in a steam reformer, more of the carbon oxides exits as carbon monoxide (CO) and this results in a more reactive synthesis gas and a more exothermic methanol synthesis reaction. The heats of reaction for the two overall synthesis reactions are:

$$3H_2 + CO_2 \Leftrightarrow CH_3OH + H_2O \quad \Delta H = -49.43 \text{ KJ/gmol}$$

$$2H_2 + CO \Leftrightarrow CH_3OH \quad \Delta H = -90.55 \text{ KJ/gmol}$$

As can be seen, almost twice as much heat is released when 1 kgmol of CO is converted into methanol as compared to $CO_2$.

The use of more reactive synthesis gas leads to smaller catalyst volumes being used, and the greater net heat of reaction gives a heat release per unit volume of catalyst which can be more than double that in a process based on steam reforming alone. Therefore providing effective cooling of the catalyst becomes more important as the carbon monoxide to carbon dioxide ratio in the synthesis gas increases.

In a simple loop arrangement using a single methanol converter, a tube-cooled converter (TCC), in which the catalyst bed is cooled by feed gas passing through open ended tubes disposed within the bed that discharge the heated gas to the catalyst, may provide sufficient cooling area for a more reactive synthesis gas e.g. from combined reforming or coal gasification, but the increased heat of reaction would mean that the circulating loop gas flow would be insufficient to carry away the reaction heat without the flow becoming excessively high. At large plant capacities, this becomes impractical due to the size implications on the loop pipework.

Gas cooled converters (GCC's), as described in the aforesaid U.S. Pat. No. 5,827,901, cool the catalyst bed by passing a synthesis gas mixture comprising the loop gas mixed with make up gas though tubes in a heat exchanger-type arrangement.

Steam raising converters (SRC's) as described in the aforesaid U.S. Pat. No. 5,631,302 in which the catalyst is present in tubes cooled by boiling water under pressure offer a useful means to remove heat from the catalyst. However, while the axial SRC offers the highest cooling factor, it makes poorer use of the vessel volume so the vessel shell is large for the quantity of catalyst that it holds. Furthermore, the cooling comes at a cost since the tubes that provide the high cooling area are numerous and are made of relatively expensive material, and the flat tubesheets are of large diameter, relatively thick and can be costly to fabricate. Accordingly small SRC reactors are desirable.

The present invention offers an improved combination of synthesis reactors from the realisation that the high cooling factor of an SRC is really only essential where the reaction rates are highest. The rate of production of methanol varies down the length of a typical catalyst bed, with the highest reaction rate near the top of the bed and therefore we have found that the high cooling factor of an SRC is only really required to around half way down the tube, and then another reactor could be used such as a TCC or GCC. This is particularly the case with coal gasification synthesis gas.

A further problem with synthesis gas, particularly coal gasification synthesis gas is that it often contains sulphur compounds that poison methanol synthesis catalysts. Desulphurisation may be accomplished using known desulphurisation materials, for example by entrapment of hydrogen sulphide using zinc oxide compositions. Other desulphurisation methods and materials may also be used, e.g. to convert organosulphur compounds to hydrogen sulphide. Desulphurisation is preferably effected at elevated temperatures, thus requiring some heating of the make up gas.

Therefore in the present invention preferably the make up gas, prior to combination with said loop gas, is heated in heat exchange with either said mixed gas containing methanol from the first synthesis reactor or said product gas, and then passed though a bed of desulphurisation material.

In the process disclosed in the aforesaid U.S. Pat. No. 5,827,901, the make up gas would have to be heated separately using the product gas stream, resulting in insufficient cooling in the second reactor using just the loop gas, thereby causing the temperature of the product gas from the second reactor to rise with the consequential reduction in conversion. In the present invention, there is preferably cooling of the mixed gas containing methanol produced in the first synthesis reactor. Where the second synthesis reactor is cooled by synthesis gas (i.e. in a GCC) this allows heat exchange with the make up gas, with the loop gas used to remove the remainder of the heat and the desired low temperature of the product gas may be restored.

In an alternative embodiment, the second reactor may be a TCC in which the entire cooled gas from the first synthesis reactor is used to cool the bed of catalyst, so ensuring that there is sufficient cooling available even though the make up gas is heated separately, using e.g. the product gas stream. The use of a TCC is further beneficial over the gas cooled reactor of U.S. Pat. No. 5,827,901 in that it is simpler and cheaper to fabricate due to the use of open topped tubes and the elimination of the upper header and all of the differential expansion problems that the gas cooled converter raises.

Accordingly, in a first preferred embodiment, the mixed gas containing methanol from the first synthesis reactor is cooled in heat exchange with said loop gas, thereby forming a heated loop gas which is mixed with desulphurised make-up gas to form the synthesis gas mixture fed to the first methanol synthesis reactor, and the make up gas, prior to combination with said heated loop gas, is heated in heat exchange with the product gas and then passed though a bed of desulphurisation material to form the desulphurised make up gas. If desired, the loop gas may be heated in heat exchange with the product gas stream as well as the mixed gas containing methanol from the first synthesis reactor. In this case, preferably the loop gas is heated using the product gas stream after the product gas stream has been used to heat the make up gas. In these embodiments, the second synthesis reactor is preferably a tube-cooled converter containing a bed of methanol synthesis catalyst in which the bed is cooled by passing the cooled mixed gas containing methanol through tubes within the bed resulting in a heated mixed gas stream, which is then passed through the bed to synthesise further methanol.

In a second preferred embodiment, the mixed gas containing methanol from the first synthesis reactor is cooled in heat exchange with make up gas, thereby forming a heated make up gas which is then passed through a desulphurisation material to form a desulphurised make up gas which is mixed with the loop gas to form the synthesis gas mixture fed to the first reactor. In this embodiment the second synthesis reactor is preferably a gas cooled converter containing a bed of methanol synthesis catalyst in which the bed is cooled by passing the loop gas through tubes within the bed resulting in a heated loop gas which is mixed with the desulphurised make up gas to form the synthesis gas mixture fed to the first reactor. Furthermore in this embodiment, preferably the loop gas is pre-heated prior to passing to the tubes of the gas cooled converter by exchanging heat with the product gas.

Furthermore, within these embodiments is also possible to add portions of the desulphurised make up gas or loop gas to the mixed gas containing methanol from the first synthesis reactor, before or after it is cooled and fed to the second synthesis reactor.

The methanol synthesis catalysts are preferably copper-containing methanol synthesis catalysts, in particular the methanol synthesis catalyst in the first and second synthesis reactors is a particulate copper/zinc oxide/alumina catalyst. Particularly suitable catalysts are Mg-doped copper/zinc oxide/alumina catalysts as described in U.S. Pat. No. 4,788,175. Different catalysts may be used in the first and second synthesis reactors.

Methanol synthesis may be effected at pressures in the range 20 to 120 bar abs and temperatures in the range 130° C. to 350° C. As the first synthesis reactor need not provide a high conversion of carbon oxides, this first reactor can be fed with a large amount of synthesis gas. Usually, the gas load for this first reactor lies in the range from 12,000 to 24,000 $Nm^3$ per hour and per $m^3$ catalyst. The first gas mixture withdrawn from the first synthesis reactor may contain 6 to 14 vol.-% methanol vapour. The product gas stream withdrawn from the second reactor typically has temperatures in the range from 180 to 250° C.

In FIG. 1, a synthesis gas 10 comprising a mixture of loop gas 12 and make up gas 14 is fed to the top of a first synthesis reactor 16 where it is passed through a plurality of catalyst filled tubes 18 that are cooled by boiling water under pressure. The catalyst is a particulate copper/zinc oxide/alumina catalyst. Boiling water under pressure is fed to the reactor via line 20 and a mixture of boiling water and steam is withdrawn via line 22 and supplied to steam drum 24. The steam drum is fed with boiler feed water and generates medium pressure steam. The methanol synthesis reaction takes place as the synthesis gas passes through the tubes 18 to form a mixed gas containing methanol vapour. The mixed gas containing methanol is collected and fed from the first reactor 16 via line 26 to the tube side of a tube and shell heat exchanger 28 where it is partially cooled. The resulting cooled mixed gas containing methanol is then fed from heat exchanger 28 via line 30 to the bottom of a second synthesis reactor 32 and passed upwards through a plurality of tubes 34 disposed within a catalyst bed. The gas is heated as it passes upwards through tubes 34. The heated gas exits the tubes 34 within the reactor above the bed and then passes down through the bed. The catalyst bed comprises a particulate copper/zinc oxide/alumina catalyst. The methanol synthesis reaction takes place as the heated gas passes through the bed forming a product gas stream. The product gas stream is collected and fed from the synthesis reactor 32 via line 36 to the tube side of a tube and shell heat exchanger 38 where it is cooled. The product gas is then fed from the heat exchanger 38 to air cooler 40 where it is further cooled and thence to the tube side of heat exchanger 42 where it is cooled with water to below the dew point of methanol, thereby causing the methanol in the product gas stream to condense. The resulting stream is fed from heat exchanger 42 via line 44 to a first separator 46 in which unreacted gases are separated from the liquid product stream. The liquid product stream is then fed via line 48 to a second separator 50 in which a flash gas 54 is separated from the crude methanol product 52.

The unreacted gases from first separator 46 are fed via line 56 to a compressor 58 and thence via line 60 to the shell side of heat exchanger 28 where they are heated and then fed as loop gas via line 12 to form the synthesis gas 10 fed to the first synthesis reactor 16. A purge is taken from line 56 via line 62 to prevent the build up of inerts.

Make up gas derived from a coal gasification process, containing hydrogen, carbon monoxide and carbon dioxide and a CO:CO2 ration >5:1, is fed via line 64 to a compressor 66 where it is compressed to the loop pressure and fed to the shell side of heat exchanger 38 where it is heated. The heated make up gas is then passed via line 68 to a desulphurisation vessel 70 containing a bed of desulphurisation material 72. The sulphur compounds present in the make up gas are removed by the desulphurisation material and the resulting desulphurised make up gas is fed from vessel 70 via line 14 to form the synthesis gas 10 fed to the first synthesis reactor 16.

Figure 2:
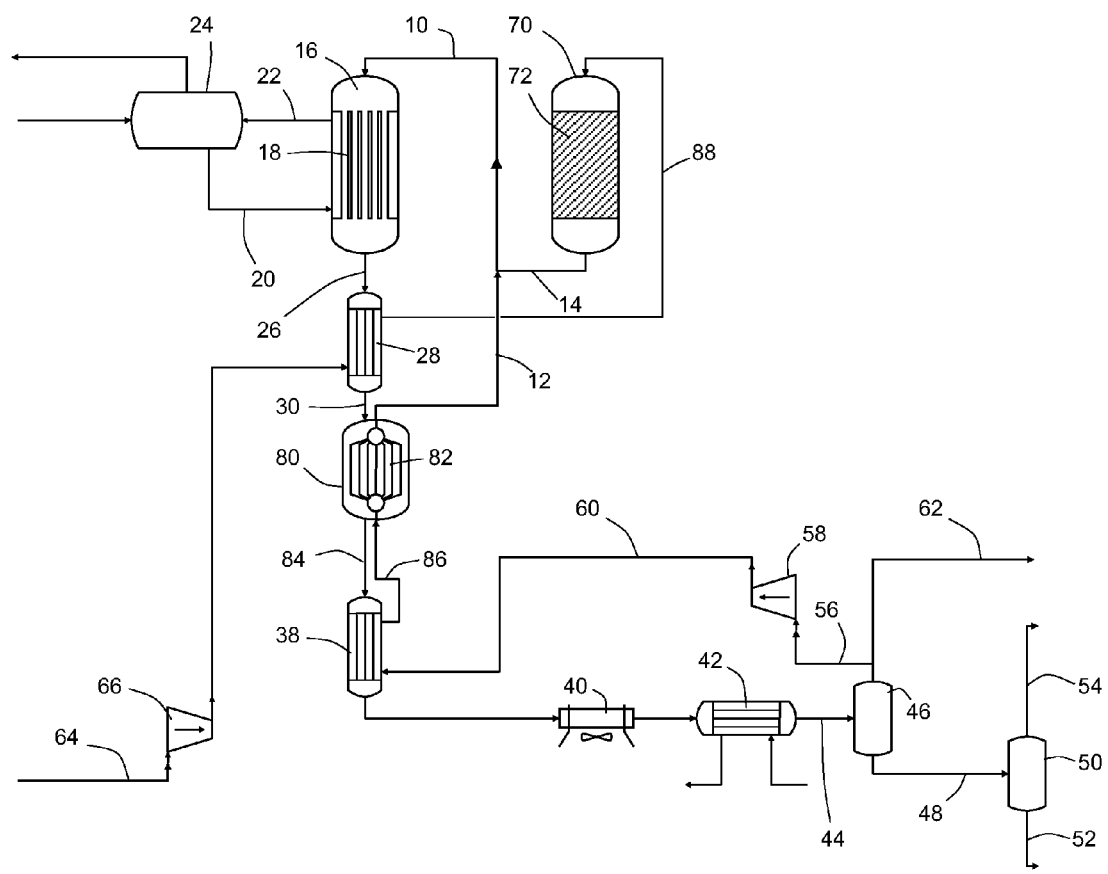
FIG. 2 depicts a flowsheet according to a further embodiment of the present invention utilising a SRC and GCC.

In FIG. 2, a synthesis gas 10 comprising a mixture of loop gas 12 and make up gas 14 is fed to the top of a first synthesis reactor 16 where it is passed through a plurality of catalyst filled tubes 18 that are cooled by boiling water under pressure. The catalyst is a particulate copper/zinc oxide/alumina catalyst. Boiling water under pressure is fed to the reactor via line 20 and a mixture of boiling water and steam is withdrawn via line 22 and supplied to steam drum 24. The steam drum is fed with boiler feed water and generates medium pressure steam. The methanol synthesis reaction takes place as the synthesis gas passes through the tubes 18 to form a mixed gas containing methanol vapour. The mixed gas containing methanol is collected and fed from the first reactor 16 via line 26 to the tube side of a tube and shell heat exchanger 28 where it is partially cooled. The resulting cooled mixed gas containing methanol is then fed from heat exchanger 28 via line 30 to the top of a second synthesis reactor 80 and passed downwards through a bed of methanol synthesis catalyst cooled by a coolant passing counter-current through a plurality of tubes 82 disposed within a catalyst bed. The catalyst bed comprises a particulate copper/zinc oxide/alumina catalyst. The methanol synthesis reaction takes place as the gas passes through the bed forming a product gas stream. The product gas stream is collected and fed from the synthesis reactor 80 via line 84 to the tube side of a tube and shell heat exchanger 38 where it is cooled. The product gas is then fed from the heat exchanger 38 to air cooler 40 where it is further cooled and thence to the tube side of heat exchanger 42 where it is cooled with water to below the dew point of methanol, thereby causing the methanol in the product gas stream to condense. The resulting stream is fed from heat exchanger 42 via line 44 to a first separator 46 in which unreacted gases are separated from the liquid product stream. The liquid product stream is then fed via line 48 to a second separator 50 in which a flash gas 54 is separated from the crude methanol product 52.

The unreacted gases from first separator 46 are fed via line 56 to a compressor 58 and thence via line 60 to the shell side of heat exchanger 38 where they are heated and then fed via line 86 to the tubes 82 of the second synthesis reactor 80, in which they are further heated and then fed as loop gas via line 12 to form the synthesis gas 10 fed to the first synthesis reactor 16. A purge is taken from line 56 via line 62 to prevent the build up of inerts.

Make up gas derived from a coal gasification process, containing hydrogen, carbon monoxide and carbon dioxide and a CO:CO2 ration >5:1, is fed via line 64 to a compressor 66 where it is compressed to the loop pressure and fed to the shell side of heat exchanger 28 where it is heated. The heated make up gas is then passed via line 88 to a desulphurisation vessel 70 containing a bed of desulphurisation material 72. The sulphur compounds present in the make up gas are removed by the desulphurisation material and the resulting desulphurised make up gas is fed from vessel 70 via line 14 to form the synthesis gas 10 fed to the first synthesis reactor 16.

Figure 3:
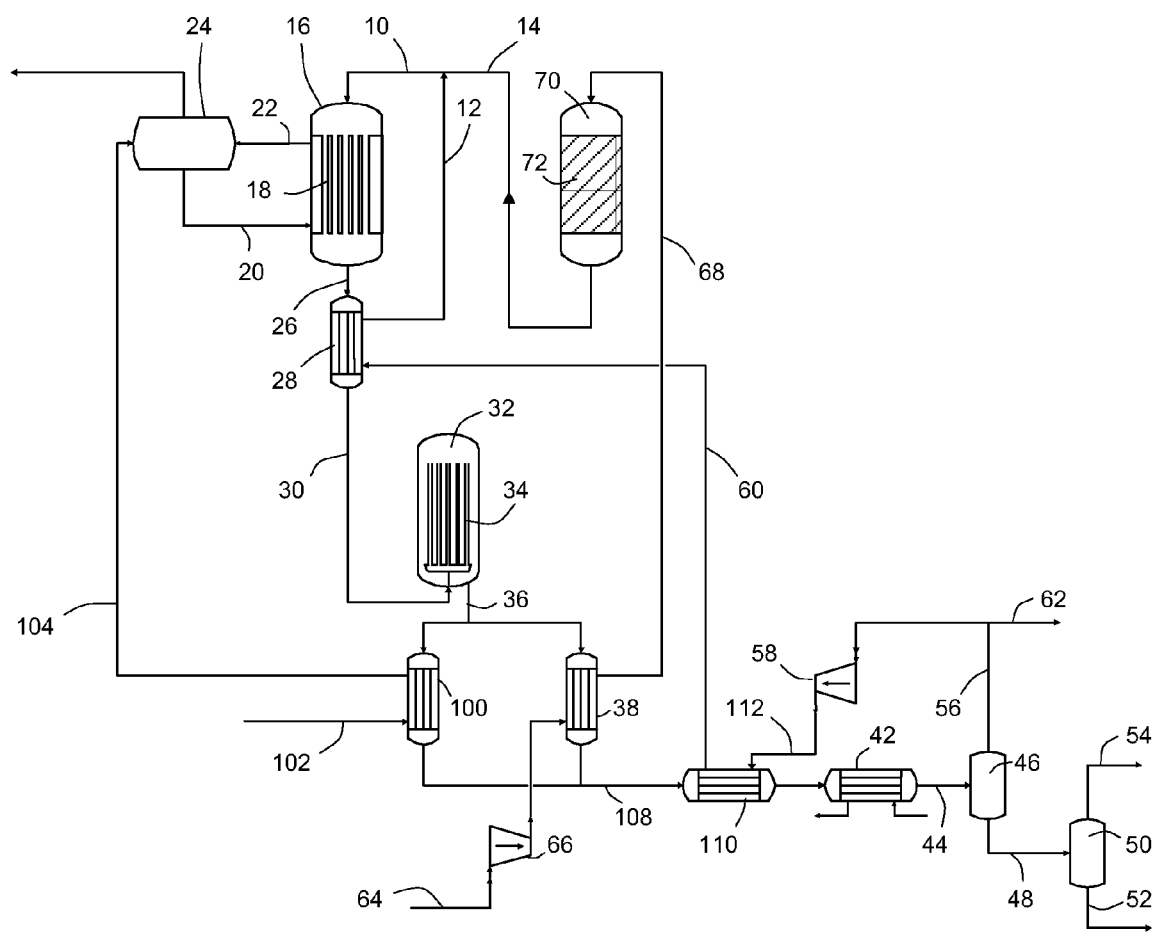
FIG. 3 depicts a flowsheet of an alternative embodiment utilising a SRC and TCC.

In FIG. 3, a synthesis gas 10 comprising a mixture of loop gas 12 and make up gas 14 is fed to the top of a first synthesis reactor 16 where it is passed through a plurality of catalyst filled tubes 18 that are cooled by boiling water under pressure. The catalyst is a particulate copper/zinc oxide/alumina catalyst. Boiling water under pressure is fed to the reactor via line 20 and a mixture of boiling water and steam is withdrawn via line 22 and supplied to steam drum 24. The steam drum is fed with heated water 104 and generates medium pressure steam. The methanol synthesis reaction takes place as the synthesis gas passes through the tubes 18 to form a mixed gas containing methanol vapour. The mixed gas containing methanol is collected and fed from the first reactor 16 via line 26 to the tube side of a tube and shell heat exchanger 28 where it is partially cooled. The resulting cooled mixed gas containing methanol is then fed from heat exchanger 28 via line 30 to the bottom of a second synthesis reactor 32 and passed upwards through a plurality of tubes 34 disposed within a catalyst bed. The gas is heated as it passes upwards through tubes 34. The heated gas exits the tubes 34 within the reactor above the bed and then passes down through the bed. The catalyst bed comprises a particulate copper/zinc oxide/alumina catalyst. The methanol synthesis reaction takes place as the heated gas passes through the bed forming a product gas stream. The product gas stream is collected and fed from the synthesis reactor 32 via line 36 to the tube side of a tube and shell heat exchanger 38 where it is cooled. A portion of the product gas stream is also fed to heat exchanger 100 where it is cooled by water 102. The resulting heated water stream 104 is fed to the steam drum 24. The cooled product gas streams from heat exchangers 100 and 38 are combined and fed via line 108 to the tube side of heat exchanger 110 and thence to the tube side of heat exchanger 42 where it is cooled with water to below the dew point of methanol, thereby causing the methanol in the product gas stream to condense. The resulting stream is fed from heat exchanger 42 via line 44 to a first separator 46 in which unreacted gases are separated from the liquid product stream. The liquid product stream is then fed via line 48 to a second separator 50 in which a flash gas 54 is separated from the crude methanol product 52.

The unreacted gases from first separator 46 are fed via line 56 to a compressor 58 and thence via line 112 to the shell side of heat exchanger 110, where they are heated and then passed via line 60 to the shell side of heat exchanger 28 where they are further heated and then fed as loop gas via line 12 to form the synthesis gas 10 fed to the first synthesis reactor 16. A purge is taken from line 56 via line 62 to prevent the build up of inerts.

Make up gas derived from a coal gasification process, containing hydrogen, carbon monoxide and carbon dioxide and a CO:CO2 ration >5:1, is fed via line 64 to a compressor 66 where it is compressed to the loop pressure and fed to the shell side of heat exchanger 38 where it is heated. The heated make up gas is then passed via line 68 to a desulphurisation vessel 70 containing a bed of desulphurisation material 72. The sulphur compounds present in the make up gas are removed by the desulphurisation material and the resulting desulphurised make up gas is fed from vessel 70 via line 14 to form the synthesis gas 10 fed to the first synthesis reactor 16.

This embodiment recycles more heat to the SRC 16, increasing steam generation and reducing the cooling duty on the downstream heat exchangers, thereby reducing cooling water consumption. The use of heat exchanger 110 also can give better control of the operating temperature in the second methanol synthesis reactor 32.

The invention claimed is:

1. A process for the synthesis of methanol comprising the steps of:
   (a) passing a synthesis gas mixture comprising a loop gas and a make-up gas through a first synthesis reactor containing a methanol synthesis catalyst, said reactor cooled by boiling water under pressure, to form a mixed gas containing methanol,
   (b) cooling the mixed gas containing methanol,
   (c) passing said cooled mixed gas containing methanol through a second synthesis reactor containing a methanol synthesis catalyst in which further methanol is synthesised to form a product gas stream,
   (d) cooling said product gas to condense methanol, and
   (e) recovering said methanol and returning unreacted gas as the loop gas to said first synthesis reactor,
   wherein the mixed gas containing methanol from the first synthesis reactor is cooled in heat exchange with either said loop gas or said make up gas.

2. A process according to claim 1 wherein the make up gas, prior to combination with said loop gas, is heated in heat exchange with either said mixed gas containing methanol from the first synthesis reactor or said product gas, and then passed through a bed of desulphurisation material to form a desulphurised make up gas.

3. A process according to claim 2 wherein (i) the mixed gas containing methanol from the first synthesis reactor is cooled in heat exchange with said loop gas, thereby forming a heated loop gas which is mixed with the desulphurised make-up gas to form the synthesis gas mixture fed to said first reactor, and (ii) the make up gas, prior to combination with said heated loop gas, is heated in heat exchange with said product gas and then passed through a bed of desulphurisation material to form said desulphurised make up gas.

4. A process according to claim 3 wherein the product gas stream from the second synthesis reactor is divided into two portions, a first portion being cooled in heat exchange with said make up gas, and a second portion in heat exchange with water, with combination of the cooled first and second portions prior to further cooling.

5. A process according to claim 3 wherein the loop gas is heated in heat exchange with the mixed gas containing methanol from the first synthesis reactor and the product gas stream after the product gas stream has been used to heat the make up gas.

6. A process according to claim 3 wherein the second synthesis reactor is a tube-cooled converter containing a bed of methanol synthesis catalyst in which said bed is cooled by passing the cooled mixed gas containing methanol through tubes within the bed resulting in a heated mixed gas stream which is then passed through said bed to synthesise further methanol.

7. A process according to claim 2 wherein the mixed gas containing methanol from the first synthesis reactor is cooled in heat exchange with make up gas, thereby forming a heated make up gas which is then passed through the desulphurisation material to form said desulphurised make up gas which is mixed with said loop gas to form the synthesis gas mixture fed to said first reactor.

8. A process according to claim 7 wherein the second synthesis reactor is a gas cooled converter containing a bed of methanol synthesis catalyst in which said bed is cooled by passing said loop gas through tubes within the bed resulting in a heated loop gas which is mixed with said desulphurised make up gas to form the synthesis gas mixture fed to said first reactor.

9. A process according to claim 8 wherein the loop gas is pre-heated prior to, passing to the tubes of the gas cooled converter by exchanging heat with the product gas.

10. A process according to claim 1 wherein the ratio of $CO:CO_2$ by volume in the make up gas is $\geq 2:1$.

11. A process according to claim 1 wherein the make up gas is a product of combined reforming, coal gasification or a refinery off-gas.

12. A process according to claim 1 wherein the methanol synthesis catalyst in the first and second synthesis reactors is a particulate copper-zinc-alumina catalyst.

13. A process according to claim 1 wherein methanol synthesis is effected at pressures in the range 20 to 120 bar abs and temperatures in the range 130° C. to 350° C.

14. A process according to claim 1 wherein the gas mixture withdrawn from the first synthesis reactor contains 6 to 14 vol.-% methanol vapour.

15. A process according to claim 1 wherein the ratio of $CO:CO_2$ by volume in the makeup gas is $\geq 5:1$.

* * * * *